(12) United States Patent
Swanson (10) Patent No.: US 10,314,734 B2
(45) Date of Patent: Jun. 11, 2019

(54) LUMBAR SUPPORT PLATE

(71) Applicant: Erick Swanson, Cleveland, OH (US)

(72) Inventor: Erick Swanson, Cleveland, OH (US)

( * ) Notice: Subject to any disclaimer, the term of this patent is extended or adjusted under 35 U.S.C. 154(b) by 0 days.

(21) Appl. No.: 15/873,385

(22) Filed: Jan. 17, 2018

(65) Prior Publication Data

US 2018/0200098 A1    Jul. 19, 2018

Related U.S. Application Data

(60) Provisional application No. 62/447,164, filed on Jan. 17, 2017, provisional application No. 62/515,580, filed on Jun. 6, 2017.

(51) Int. Cl.
*A61F 5/02* (2006.01)
*F41H 5/02* (2006.01)
*F41H 1/02* (2006.01)

(52) U.S. Cl.
CPC ............ *A61F 5/028* (2013.01); *F41H 5/023* (2013.01); *F41H 1/02* (2013.01)

(58) Field of Classification Search
CPC ................................. A61F 5/028; F41H 5/023
USPC ..... 2/2.5; 89/36.05, 36.02, 36.01; 114/14, 9, 114/10
See application file for complete search history.

(56) References Cited

U.S. PATENT DOCUMENTS

| | | | | |
|---|---|---|---|---|
| 1,398,682 A * | 11/1921 | Dragic | ...................... | F41H 1/02 109/82 |
| 1,739,112 A * | 12/1929 | Wisbrod | ................... | F41H 1/02 109/82 |
| 2,052,684 A * | 9/1936 | Elliott | ...................... | F41H 1/02 109/82 |
| 2,819,759 A * | 1/1958 | Goodloe | ............ | A41D 31/0027 160/330 |
| 3,061,839 A * | 11/1962 | Foster | ...................... | F41H 1/02 2/2.5 |
| 5,127,897 A | 7/1992 | Roller | | |
| 5,487,498 A | 1/1996 | Gleason | | |
| 5,753,847 A * | 5/1998 | Middione | ............... | F41H 7/035 89/36.02 |
| 5,780,761 A * | 7/1998 | Musante | ................. | F41H 7/035 89/36.02 |
| 6,159,590 A * | 12/2000 | Kim | ...................... | A61B 42/10 2/159 |
| 7,546,795 B1 * | 6/2009 | Munson, Jr. | .............. | F41H 5/00 89/36.02 |
| 7,770,233 B2 * | 8/2010 | Haskell | ................ | A41D 13/015 2/69 |
| 8,572,762 B2 | 11/2013 | Herbener et al. | | |
| 8,905,957 B1 | 12/2014 | Kozersky | | |
| 9,486,654 B1 | 11/2016 | Carpenter et al. | | |
| 2009/0282595 A1 | 11/2009 | Branson et al. | | |
| 2010/0095832 A1 * | 4/2010 | Gabrys | ..................... | B32B 3/18 89/36.02 |
| 2011/0035855 A1 | 2/2011 | Gewant | | |
| 2012/0180178 A1 | 7/2012 | Gallo | | |
| 2014/0135673 A1 | 5/2014 | Cohen et al. | | |

* cited by examiner

*Primary Examiner* — Reginald S Tillman, Jr.
(74) *Attorney, Agent, or Firm* — Fay Sharpe LLP (57) ABSTRACT

A lumbar support system and device is disclosed herein which includes a lumbar support plate. The lumbar support plate may be incorporated or used in conjunction with a body armor protective garment.

20 Claims, 7 Drawing Sheets

LUMBAR SUPPORT PLATE

CROSS-REFERENCE TO RELATED APPLICATIONS

This application claims priority from U.S. Provisional Application Ser. No. 62/447,164, filed Jan. 17, 2017; and 62/515,580, filed on Jun. 6, 2017. The disclosures of these U.S. Provisional Patent Applications are herein incorporated in their entirety by reference thereto.

BACKGROUND

The present disclosure relates to a lumbar support plate incorporated or used in conjunction with an antiballistic garment or protective body armor type gear. It finds particular application for use in conjunction with gear or garments worn by protective forces, such as bullet-proof vests worn by police officers.

The technology of body armor for personal protection has progressed greatly in recent years. For example, new materials have been devised which make significant improvements in the protection offered by antiballistic garments or protective body armor type gear. However, even with the advantages provided through use of these new materials (e.g., Kevlar, ceramic, and other ballistic grade materials), the wearer must still bear the physical weight of the garment while maintaining combat effectiveness. Combat effectiveness may be impaired if the antiballistic garments or protective body armor type being worn cause discomfort to the user's body. That is, the neck, shoulders, and back of a user often carry the weight of this protective gear, and injury or discomfort to these body parts can further be exacerbated by poor posture.

Accordingly, there is a need for a device used in conjunction with antiballistic garments and/or protective body armor type gear which reduces the discomfort and/or risk of injury to users of such gear. Such a device may achieve this by redistributing the weight of the garment off body parts that are more susceptible to fatigue, such as the shoulders and neck. The device may also improve the posture of the wearer, further reducing discomfort and/or risk of fatigue or injury.

BRIEF DESCRIPTION

Disclosed in various embodiments are lumbar support systems and devices that include a lumbar support plate. The lumbar support plate may be incorporated or used in conjunction with a body armor protective garment.

In some embodiments, a lumbar support device includes a support plate including a first end, a second end, and a convexly curved surface. A curved hook portion is located at the first end of the support plate and a flat portion is located at the second end of the support plate. The convexly curved surface is shaped to provide lumbar support, the curved hook portion is configured to mate with a component of an associated garment, and the flat portion is configured to engage the component of the associated garment. The lumbar support device can be used in an associated body armor protection system.

In particular embodiments, the associated garment is a body armor garment which uses the lumbar support device. The component of the associated body armor garment can be a protective plate. In such embodiments, the curved hook portion of the support plate is placed in overlapping relationship with a bottom edge of the protective plate to provide a mated configuration therewith. The flat portion of the support plate pushes against the protective plate in the mated configuration.

In other embodiments, the support plate has a length between the first and second ends of from about 6 inches to about 12 inches, a width from about 6 inches to about 10 inches, and a thickness of from about $1/32$ of an inch to about $1/8$ of an inch, including about $1/16$ of an inch. In particular embodiments, the length of the support plate is about 10 inches or about 8.5 inches, the width is about 8 inches, and the thickness is about $1/16$ of an inch. The convexly curved surface of the support plate has a peak curve height in some embodiments of from about 1 inch to about 3 inches, including about 2 inches.

In particular embodiments, the support plate can further include one or more additional features. Such additional features include one or more ridge portions configured to reinforce or add extra stiffness to the support plate, one or more perforations which aid in the ventilation and dissipation of heat generated between the users back and the corresponding body armor system being worn, and/or one or more open portions in the support plate in order to reduce material costs and/or weight.

In some embodiments, the lumbar support plate has a peak curve height that is located closer in distance to the first end of the support plate. In other embodiments, the peak curve height is located closer in distance to the second end of the support plate. In some particular embodiments, the lumbar support plate has a peak curve height that is located centrally between the first and second ends of the support plate.

According to additional embodiments, the curved hook portion of the support plate has a resting point on a generally flat plane that is collinear with a resting point of the flat portion. In other additional embodiments, the resting point of the curved hook portion is offset from the resting point of the flat portion.

Also disclosed in several embodiments herein is a body armor protection system which includes a lumbar support plate having a first end, a second end, and a convexly curved surface, the first end including a curved hook portion and the second end including a flat portion. The convexly curved surface is shaped to provide lumbar support. A protective body armor garment includes a pocket region and a protective plate contained within the pocket region. The protective plate is adapted to protect a user's back. The lumbar support plate and the protective body armor garment have a mated configuration where the lumbar support plate is disposed between the protective back plate and the user's back, with the convex curved surface being oriented toward the user's back, the curved hook portion being placed in overlapping relationship with a bottom edge of the protective back plate, and the flat portion pushes against the protective back plate.

Additionally disclosed herein are various embodiments for a lumbar support device which includes a support plate having a first end, a second end, and a convexly curved surface. The convexly curved surface has a peak curve height located between the first and second end of the support plate. A curved hook portion is located at the first end of the support plate and has a resting point on a generally flat plane. A flat portion is located at the second end of the support plate and has a resting point on the generally flat plane that is collinear with the resting point of the curved hook portion. The convexly curved surface is shaped to provide lumbar support, the curved hook portion is configured to mate with a component of an associated garment, and the flat portion is configured to engage the component of the associated garment.

These and other non-limiting aspects of the present disclosure are further discussed herein.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps With reference FIGS. 1-3, a lumbar support system 100 is shown which includes a lumbar support device. The device includes a lumbar support plate 102 that has a convex curved outer surface 104 and an opposing concave inner surface 106. The lumbar support plate extends in a generally curvilinear manner between a first end 108 and a second end 110. The first end 108 includes a curved hook portion 112 for mating with an associated component of a corresponding body armor protective garment (not shown). The second end 110 includes a generally flat portion 114 which engages with the same associated component of the corresponding body armor protective garment as curved hook portion 112.

Figure 1:
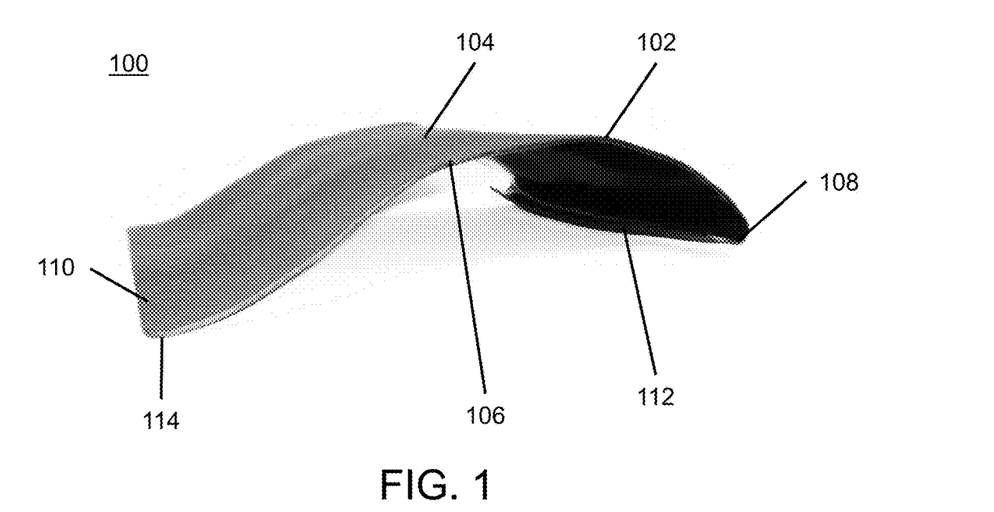
FIG. 1 is a perspective view picture of a lumbar support plate to be used in connection with a protective body armor garment in accordance with one embodiment of the present disclosure.
Figure 2:
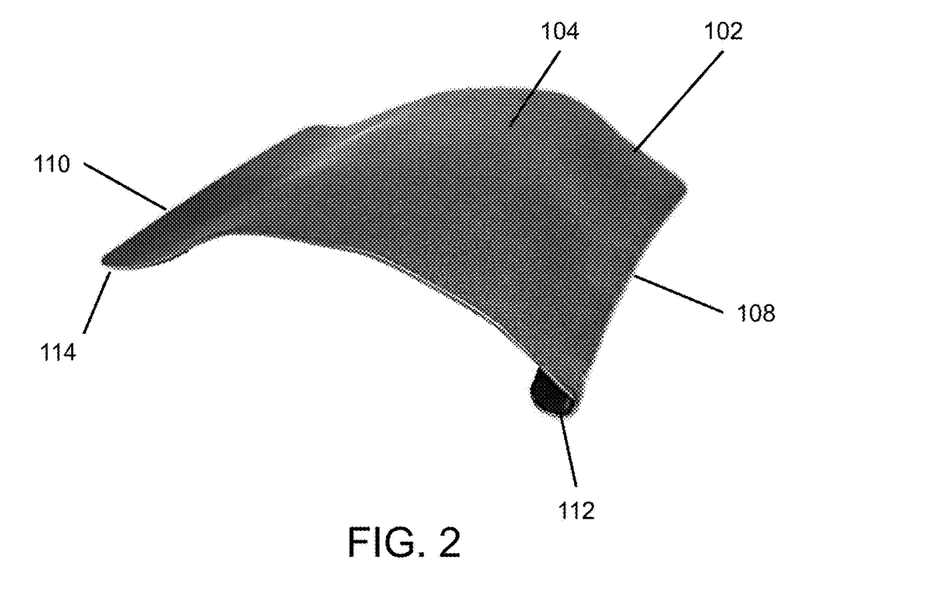
FIG. 2 is a top perspective view picture showing additional aspects of the lumbar support plate pictured in FIG. 1.
Figure 3:
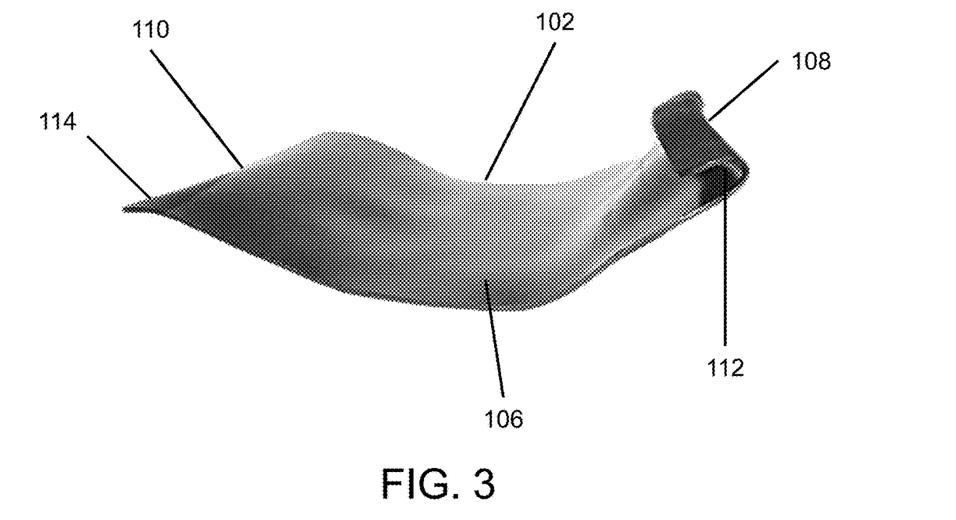
FIG. 3 is a bottom perspective view picture showing additional aspects of the lumbar support plate pictured in FIG. 1.

The convex curved outer surface 104 of the lumbar support plate 102 is preferably shaped to compliment the lumbar region of the user or wearer's back (not shown) and to provide lumbar support. The shape of the lumbar support plate 102 is preferably formed to provide lumbar support to a wide variety of users.

Figure 4:
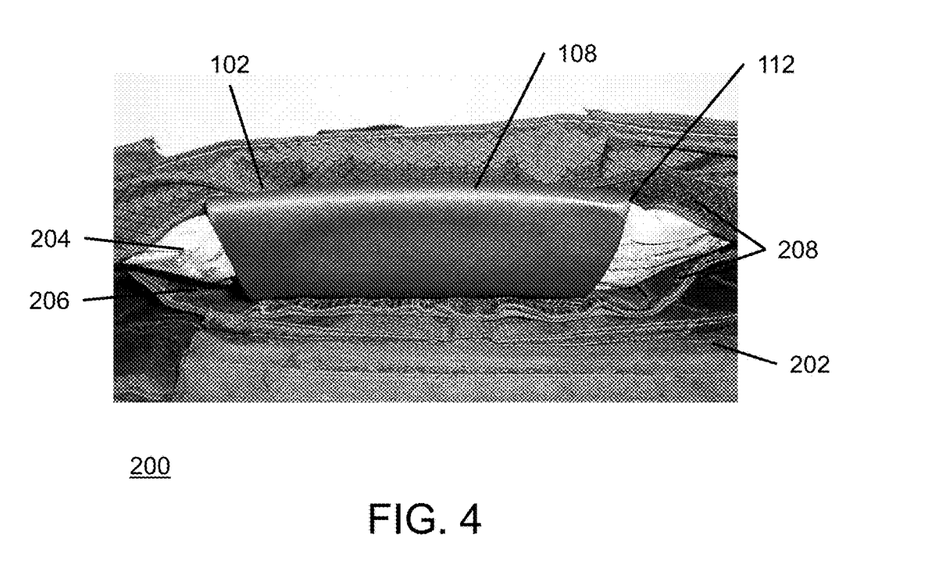
FIG. 4 is a rear view picture showing the lumbar support plate of FIG. 1 in a mated configuration with an associated protective body armor garment.
Figure 5:
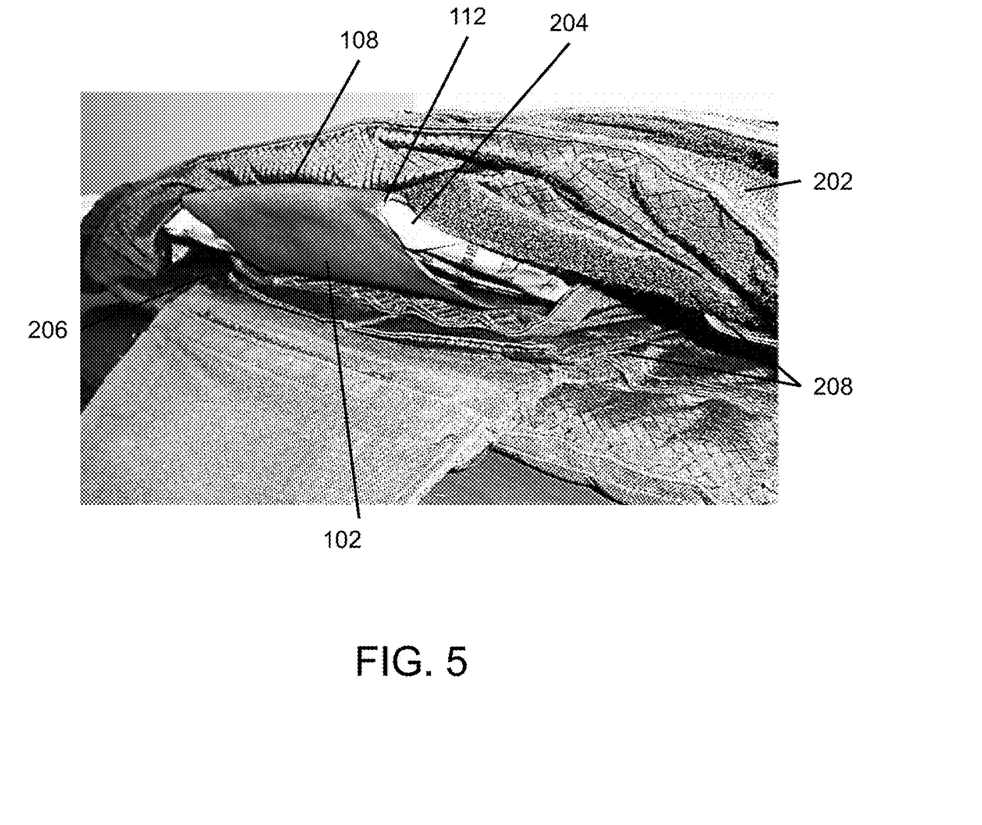
FIG. 5 is a rear perspective view showing additional aspects of the mated lumbar support plate and protective body armor garment pictured in FIG. 4.

With reference to FIGS. 4 and 5, the lumbar support plate 102 is pictured in a mated configuration with a corresponding body armor protection system 200. The body armor protection system 200 includes a protective body armor garment 202, such as a bullet-proof vest or any garment that helps absorb the impact and reduce or stop penetration to the body from firearm-fired projectiles and shrapnel from explosions, and is generally worn on the torso. The garment 202 generally includes numerous protective elements, such as portions made from layers of high tensile strength fibers such as Kevlar or ceramic or metal plates which are inserted into the protective garment 202. For example, protective plate 204 is placed within a pocket region 206 of the protective garment for protecting a user or wearer's back (not shown). The protective back plate 204 can be contained within the pocket 206 by any suitable means, including hook and loop type fasteners 208.

As shown in FIGS. 4 and 5, when it is desired to use the lumbar support plate 102, the plate is easily inserted into the pocket region 206 of the protective garment 202. Typically, the pocket 206 is selectively positioned along a major axis of a torso-encircling region of the protective garment 202 so as to be placed in contact with the lumbar region of user or wearer of the protective garment. The support plate 102 is generally disposed between the protective back plate 204 and the back of the user or wearer, with the convex curved surface 104 being generally oriented inward with respect to the protective garment 202, i.e., toward the back of the user or wearer. The curved hook portion 112 is placed in overlapping relationship with a bottom edge of the protective back plate 204. The overlapping relationship of the curved hook portion 112 with the back plate 204 helps to maintain the lumbar support plate 102 in the appropriate position for maintaining lumbar support while the protective garment 202 is being worn. Moreover, when the protective garment 202 is in use, the user's back applies a force to the convex curved surface 104, thereby causing the generally flat portion 114 of the lumbar support plate 102 to push against the back plate 204. This interaction of forces also helps to maintain the lumbar support plate 102 in proper position within the pocket 206 for maintaining lumbar support.

Figure 6:
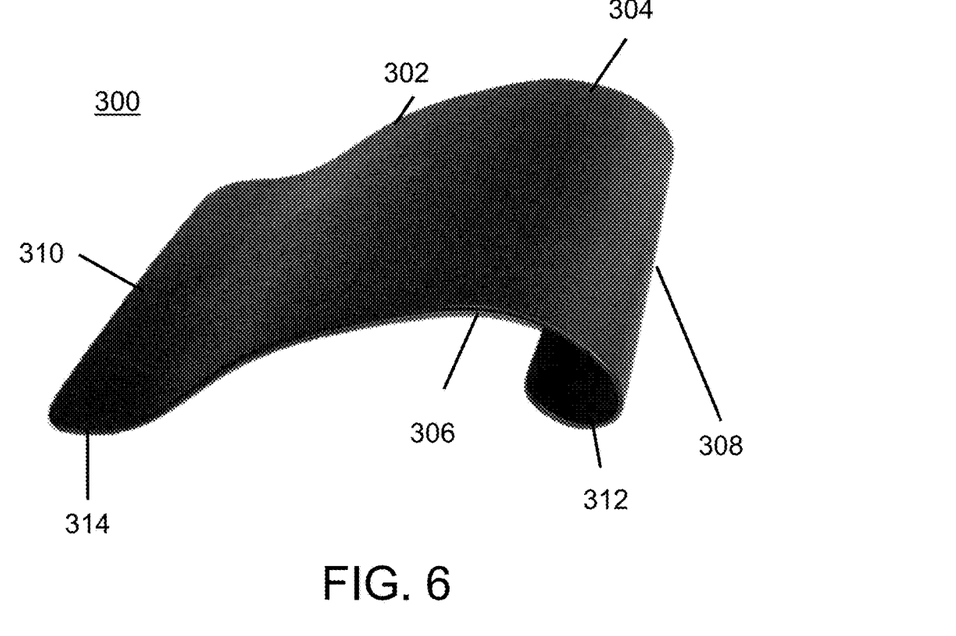
FIG. 6 is a perspective view picture of a lumbar support plate to be used in connection with a protective body armor garment in accordance with another embodiment of the present disclosure.
Figure 7:
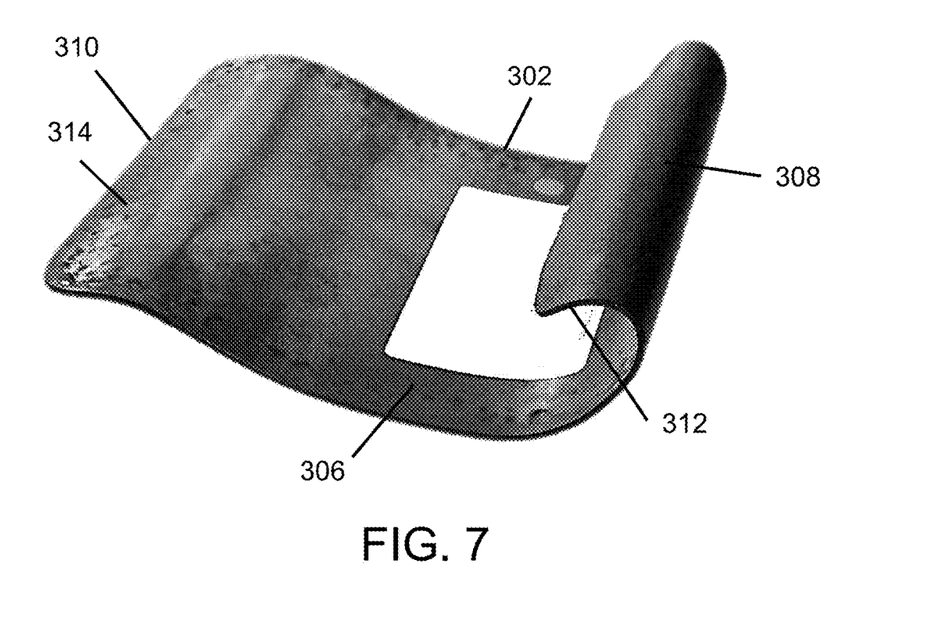
FIG. 7 is a bottom perspective view picture showing additional aspects of the lumbar support plate pictured in FIG. 6.

With reference to FIGS. 6-7, a second embodiment of a lumbar support system 300 is shown which includes a lumbar support device. The device includes a lumbar support plate 302 has a convex curved outer surface 304 and an opposing concave inner surface 306. The lumbar support plate extends in a generally curvilinear manner between a first end 308 and a second end 310. The first end 308 includes a curved hook portion 312 for mating with an associated component of a corresponding body armor protective garment (not shown). The second end 310 includes a generally flat portion 314 which engages with the same associated component of the corresponding body armor protective garment as curved hook portion 312.

The convex curved outer surface 302 of the lumbar support plate 302 is preferably shaped to compliment the lumbar region of the user or wearer's back (not shown) and to provide lumbar support. The shape of the lumbar support plate 302 is preferably formed to provide lumbar support to a wide variety of users.

Figure 8:
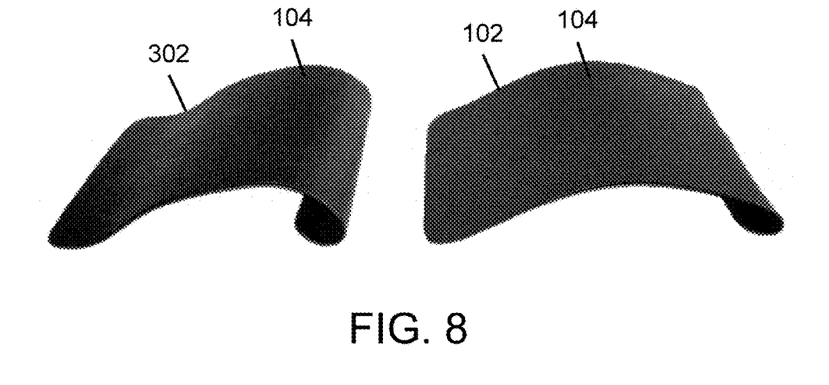
FIG. 8 is a side-by-side perspective view comparing the first embodiment of the lumbar support plate pictured in FIG. 1 with the second embodiment of the lumbar support plate pictured in FIG. 6.
Figure 9:
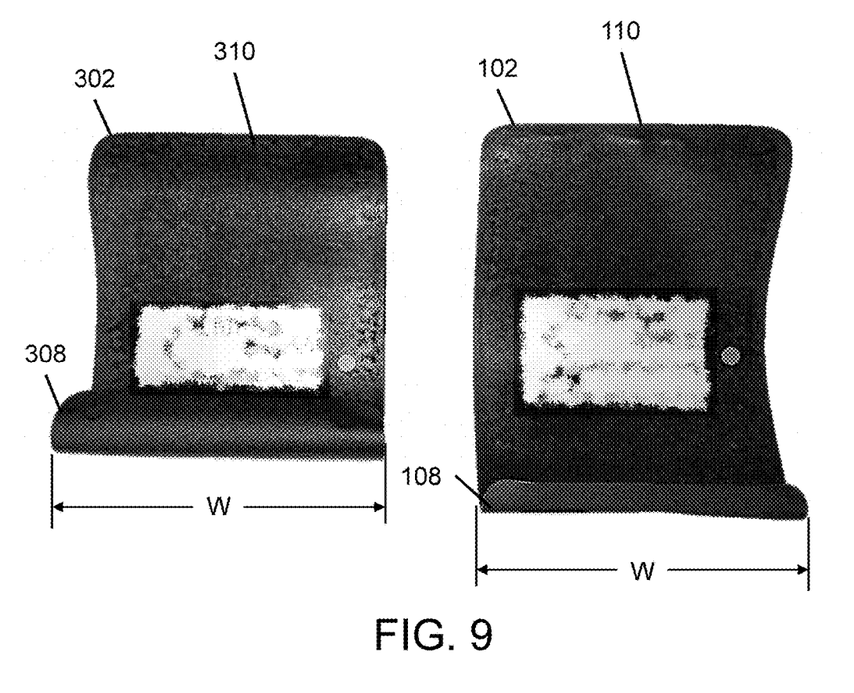
FIG. 9 is a bottom side-by-side perspective view comparing the first embodiment of the lumbar support plate pictured in FIG. 1 with the second embodiment of the lumbar support plate pictured in FIG. 6.

The lumbar support system 300 illustrated in FIGS. 6-7 is substantially similar to the lumbar support system 100 illustrated in FIGS. 1-3. However, as shown in FIG. 8, lumbar support plate 302 has a convex outer surface 304 with a varying degree of curvature that quickly changes over its length compared to the convex outer surface 104 of lumbar support plate 102. That is, the convex outer surface 104 of support plate 102 has a varying degree of curvature that gradually changes over its length. Moreover, as shown in FIG. 9, the distance between first and second ends 308, 310 of lumbar support plate 302 is shorter than the distance between first and second ends 108, 110 of lumbar support plate 102. In other words, lumbar support plate 302 is shorter than lumbar support plate 102.

FIG. 9 also shows that support plates 102, 302 have a width W that, in some embodiments, is approximately the same. In particular embodiments, the width W is from about 6 inches to about 10 inches, including from about 7 to about 9 inches. In more particular embodiments, the width W is about 8 inches. However, lumbar support plates 102, 302 can each have a different width as desired without departing from the scope of the present disclosure. A particular width may be desired, for example, depending on the type/size of the corresponding body armor protection system in which the support plate is inserted. A specific width may also be desired depending on the size of the user wearing the corresponding body armor protection system.

Despite these differences, it should be understood from the present disclosure that, regarding the mating configuration with a corresponding body armor protection system described above and shown in FIGS. 4 and 5, lumbar support plate 302 operates in substantially the same manner as lumbar support plate 102.

Figure 10:
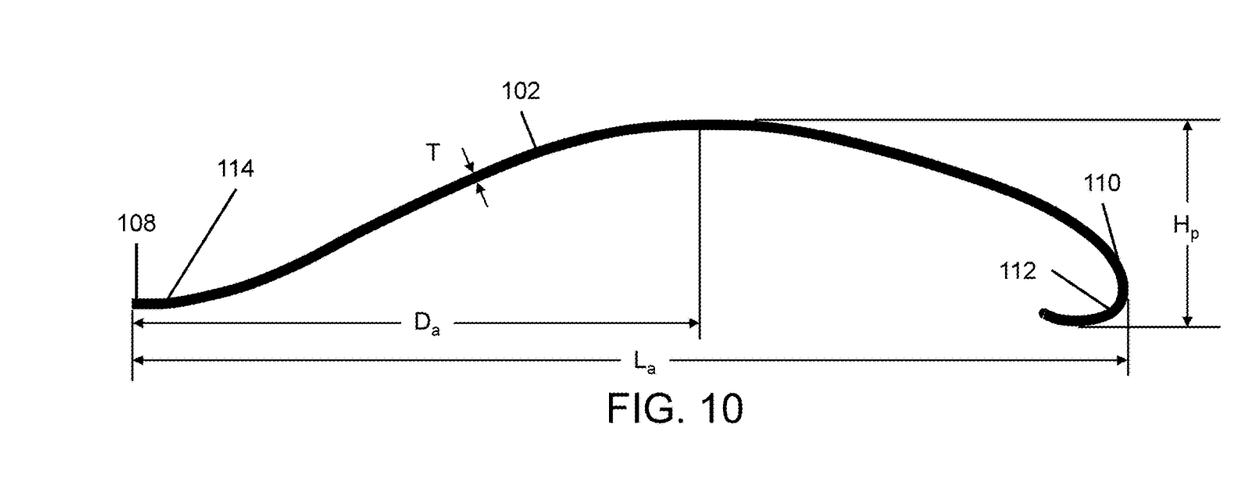
FIG. 10 is an illustration of a side profile view of the first embodiment of the lumbar support plate pictured in FIG. 1.
Figure 11:
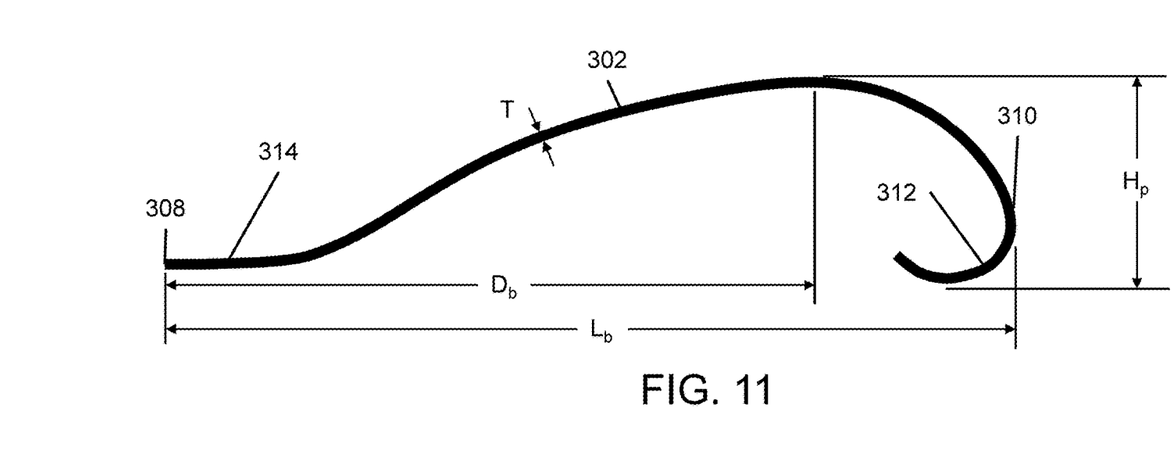
FIG. 11 is an illustration of a side profile view of the second embodiment of the lumbar support plate pictured in FIG. 6.

The differences and similarities between support plates 102 and 302 are more particularly shown in the show side profile views illustrated in FIGS. 10-11. First, as mentioned above, support plates 102, 302 have different lengths. Support plate 102 has a length $L_a$, and support plate 302 has a length $L_b$, which is generally shorter than length $L_a$. In some embodiments, the length $L_a$ of support plate 102 is from about 8 to about 12 inches long. In particular embodiments, support plate 102 has a length $L_a$ of about 10 inches. By comparison, in some embodiments the length $L_b$ of support plate 302 is from about 6 inches to about 10 inches. In particular embodiments, support plate 302 has a length $L_b$ of about 8.5 inches.

Second, as mentioned above, support plates 102 and 103 have degrees of curvature that vary differently over their respective lengths $L_a$ and $L_b$. As illustrated in FIG. 10, lumbar support plate 102 has a peak curve height $H_p$ at a distance $D_a$ from the first end 108. In some embodiments, the peak curve height distance $D_a$ of support plate 102 is from about 4 inches to about 7 inches away from the first end 108. In particular embodiments, the peak curve height distance $D_a$ is about 5.5 inches away from the first end 108.

As illustrated in FIG. 11, lumbar support plate 302 also has a peak curve height $H_p$ at a distance $D_b$ from the first end 308. In some embodiments, the peak curve height distance $D_b$ of support plate 302 is from about 4 inches to about 7 inches away from the first end 308. In particular embodiments, the peak curve height distance $D_b$ is about 6.5 inches away from the first end 308.

Accordingly, as shown in FIGS. 10 and 11, the support plate 102 may reach its peak curve height $H_p$ at a shorter distance than support plate 302. However, after the peak curve height, the support plate 102 descends toward its second end 110 over a longer distance compared with support plate 302 (i.e., descends more gradually toward its second end). The distance which support plate 302 descends after its peak curve height $H_p$ is comparatively shorter (i.e., descends towards its second end 310 more rapidly) than support plate 102.

In other words, the embodiment of support plate 102 has a peak curve height that is closer to the flat portion 114 of the first end 108 compared with the embodiment of support plate 302. In the embodiment of support plate 302, the peak curve height is closer to the curved hook portion 312 of the second end 310 and farther from the flat portion 314 of the first end 308. However, the location of the peak curve height of both lumbar support plates 102, 302 can be located at any desired distance from either the first ends 108, 308 or the second ends 110, 310 without departing from the scope of the present disclosure. For example, the peak curve height may be centrally located between the first and second ends 108, 308 and 110, 310, respectively, of support plates 102, 302.

The different aspects between lumbar support plates 102 and 302 (i.e., different degrees of curvature over their length, different lengths) may be desired for various reasons. The shorter lumbar support plate 302 may be preferable to the longer lumbar support plate 102 when, for example, a) the corresponding body armor system uses a smaller protective back plate such that a shorter lumbar support plate is required; b) the body armor is dimensioned such that its lumbar region interacts with the users back at a different location; or, c) a particular user prefers a greater amount of lumbar support (i.e., the degree of curvature of the convex outer surface extends over a shorter length.

FIGS. 10 and 11 also illustrate some similarities between lumbar support plates 102 and 302. In particular, both support plates 102, 302 have a peak curve height $H_p$ that, in some embodiments, is approximately the same despite being located at different distances from respective first ends 108, 308. In particular embodiments, the peak curve height $H_p$ is from about 1 to about 3 inches. In more particular embodiments, the peak curve height $H_p$ is about 2 inches. However, lumbar support plates 102, 302 can each have a different peak curve height as desired without departing from the scope of the present disclosure. A particular peak curve height may be desired, for example, depending on the degree of lumbar support a particular user requires (i.e., higher peak curve height equals greater lumbar support, lower peak curve height equals less lumbar support).

FIGS. 10 and 11 also show that support plates 102, 302 have a thickness T that, in some embodiments, is approximately the same. In particular embodiments, the thickness T is from about 1/32 of an inch to about 1/8 of an inch. In more particular embodiments, the thickness T is about 1/16 of an inch. However, lumbar support plates 102, 302 can each have a different thickness as desired without departing from the scope of the present disclosure. A particular thickness may be desired, for example, depending on the type of material used to form the support plate, or on the desired degree of flexibility.

FIGS. 10 and 11 further illustrate that when support plates 102, 302 are resting along/against a flat plane, the curvilinear surface of both support plates is such that the resting point of flat portions 114, 314 at the first ends 108, 308 are collinear with the resting point of curved hook portions 112, 312 at the second ends 110, 310. In other words, the resting points of the support plates 102, 302 are configured to be aligned on a flat plane. However, these resting points of lumbar support plates 102, 302 can be configured to offset from one another without departing from the scope of the present disclosure. An offset configuration may be desired, for example, depending on the type/size of the corresponding body armor protection system in which the support plate is inserted. An offset configuration may also be desired depending on the degree of lumbar support preferred by a particular user.

The lumbar support plates 102, 302 described above and shown in the corresponding figures can be formed from a flexible material that is pliable to automatically adjust to the contour of a user's lumbar region. The material from which lumbar support plates 102, 302 are formed can include plastic or metal or any other suitable material which will provide the requisite lumbar support for a user, flexibility, strength, and durability for use in protective body armor type garments. The lumbar support plates 102, 302 can be formed by any process known to those having skill in the art, however, exemplary processes include injection molding and thermal molding of raw sheet material.

Figure 12:
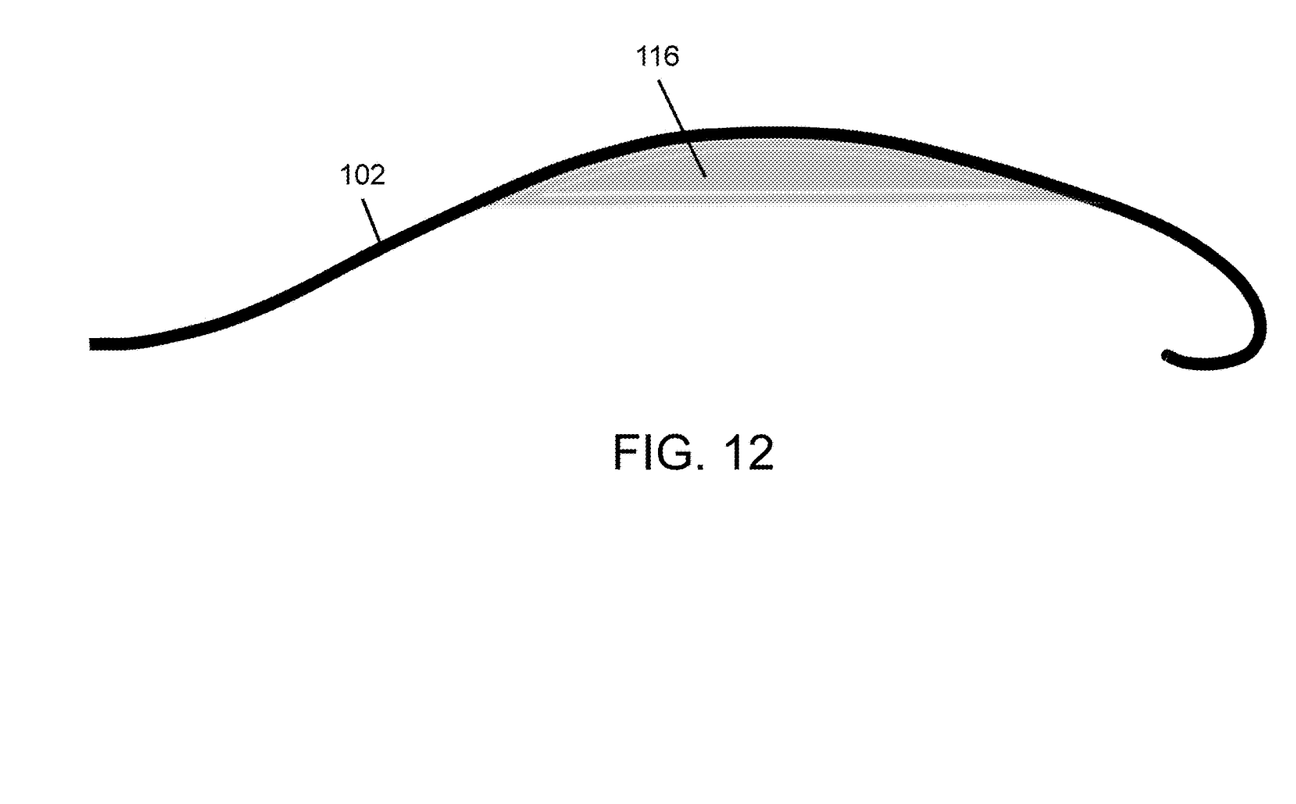
FIG. 12 is an illustration of a side profile view of the first embodiment of the lumbar support plate pictured in FIG. 1 which shows one or more ridge features adapted to reinforce or add stiffness to the support plate.

The lumbar support plates 102, 302 can include additional features without departing from the scope of the present disclosure. For example, as shown in FIG. 12, lumbar support plate 102 can include one or more spine, rib or ridge portions 116. The one or more spine, rib or ridge portions 116 can be added to reinforce the support plate or to add extra stiffness as desired and depending on the degree of lumbar support preferred by a particular user. The one or more spine, rib or ridge portions 116 can optionally be formed as an insert which attaches to the support plate, or integrally formed therewith. Moreover, while the one or more spine, rib or ridge portions 116 illustrated in FIG. 12 are shown as being disposed approximately under the peak of support plate 102, this location is only exemplary, and the one or more spine, rib or ridge portions can be disposed in any suitable location without departing from the scope of the present disclosure. In addition, while FIG. 12 illustrates the one or more spine, rib or ridge portions 116 as being provided with support plate 102, the present disclosure is not limited thereto. That is, the one or more spine, rib or ridge portions 116 could also be provided with support plate 302.

As another example of additional features, lumbar support plates 102, 302 can include one or more perforations (not shown) which aid in the ventilation and dissipation of heat generated between the users back and the corresponding body armor system being worn. Other exemplary features may include the lumbar support plates 102, 302 having open portions or portions of removed material in one or more locations. For example, the lumbar support plates 102, 302 may be formed without one or more central portions or sections in order to reduce material costs and/or weight.

It will be recognized that the lumbar support plates 102, 302 may be adapted for use on any elongate, torso-encircling member. Such torso-encircling members are well known to those having skill in the art and may include, but not be limited to, vests, body belts, harnesses, etc.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A lumbar support device comprising:
   a support plate configured to be inserted into an associated garment, the support plate including a first end, a second end, and a convexly curved surface oriented inward with respect to the associated garment,
   a curved hook portion located at the first end of the support plate, and
   a flat portion located at the second end of the support plate,
   wherein the convexly curved surface is shaped to provide lumbar support, the curved hook portion is configured to mate with a component of the associated garment, the flat portion is configured to engage the component of the associated garment.

2. A body armor protection system which uses the lumbar support device of claim 1.

3. The lumbar support device of claim 1, wherein the associated garment is a body armor garment.

4. The lumbar support device of claim 3, wherein the component of the associated body armor garment is a protective plate.

5. The lumbar support device of claim 4, wherein the curved hook portion of the support plate is placed in overlapping relationship with a bottom edge of the protective plate to provide a mated configuration therewith.

6. The lumbar support device of claim 5, wherein the flat portion of the support plate pushes against the protective plate in the mated configuration.

7. The lumbar support device of claim 1, wherein the support plate has a length between the first and second ends of from about 6 inches to about 12 inches.

8. The lumbar support device of claim 7, wherein the length of the support plate is about 10 inches.

9. The lumbar support device of claim 7, wherein the length of the support plate is about 8.5 inches.

10. The lumbar support device of claim 1, wherein the support plate has a width from about 6 inches to about 10 inches, including about 8 inches.

11. The lumbar support device of claim 1, further comprising one or more ridge portions configured to reinforce or add extra stiffness to the support plate.

12. The lumbar support device of claim 1, wherein the convexly curved surface of the support plate has a peak curve height of from about 1 inch to about 3 inches, including about 2 inches.

13. The lumbar support device of claim 12, wherein the peak curve height is located closer in distance to the first end of the support plate.

14. The lumbar support device of claim 12, wherein the peak curve height is located closer in distance to the second end of the support plate.

15. The lumbar support device of claim 12, wherein the peak curve height is located centrally between the first and second ends of the support plate.

16. The lumbar support device of claim 1, wherein the support plate has a thickness of from about $1/32$ of an inch to about $1/8$ of an inch, including about $1/16$ of an inch.

17. The lumbar support device of claim 1, wherein the curved hook portion of the support plate has a resting point on a generally flat plane that is collinear with a resting point of the flat portion.

18. The lumbar support device of claim 17, wherein the resting point of the curved hook portion offset from the resting point of the flat portion.

19. A body armor protection system comprising:
   a protective body armor garment including a pocket region and a protective plate contained within the pocket region, wherein the protective plate is adapted to protect a user's back, and,
   a lumbar support plate configured to be inserted into the pocket region of the protective body armor garment and behind the protective plate, the lumbar support plate having a first end with a curved hook portion, a second end having a flat portion, a convexly curved surface oriented to face the inside of the protective body armor garment, and an opposing concavely curved surface oriented to face the protective plate, and,
   a mated configuration wherein the curved hook portion of the first end of the lumbar support plate is placed in overlapping relationship with a bottom edge of the protective back plate, and the flat portion of the second end of the lumbar support plate engages the protective back plate.

20. A lumbar support device comprising:
   a support plate configured to mate with a component of an associated garment, the support plate including a first end, a second end, and a convexly curved surface oriented inward with respect to the associated garment and an opposing concavely curved surface oriented to face the component of the associated garment, the convexly curved surface having a peak curve height located between the first and second end of the support plate,
   a curved hook portion located at the first end of the support plate, the curved hook portion having a resting point on a generally flat plane, and
   a flat portion located at the second end of the support plate, the flat portion having a resting point on the generally flat plane that is collinear with the resting point of the curved hook portion,
   wherein the convexly curved surface is shaped to provide lumbar support, the curved hook portion is configured to mate with the component of the associated garment, the flat portion is configured to engage the component of the associated garment.

* * * * *